(12) United States Patent
Zhang et al.

(10) Patent No.: US 8,692,032 B2
(45) Date of Patent: *Apr. 8, 2014

(54) METHODS OF USING TUNGSTEN CARBIDE CATALYSTS IN PREPARATION OF ETHYLENE GLYCOL

(75) Inventors: Tao Zhang, Dalian (CN); Na Ji, Dalian (CN); Mingyuan Zheng, Dalian (CN); Aiqin Wang, Dalian (CN); Yuying Shu, Dalian (CN); Xiaodong Wang, Dalian (CN); Jingguang Chen, Dalian (CN)

(73) Assignee: Dalian Institute of Chemical Physics, Chinese Academy of Sciences, Dalian, Liaoning (CN)

( * ) Notice: Subject to any disclaimer, the term of this patent is extended or adjusted under 35 U.S.C. 154(b) by 38 days.

This patent is subject to a terminal disclaimer.

(21) Appl. No.: 13/539,041

(22) Filed: Jun. 29, 2012

(65) Prior Publication Data

US 2012/0283487 A1 Nov. 8, 2012

Related U.S. Application Data

(62) Division of application No. 12/734,763, filed as application No. PCT/CN2008/072892 on Oct. 31, 2008, now Pat. No. 8,338,326.

(30) Foreign Application Priority Data

Aug. 14, 2008 (CN) .......................... 2008 1 0012830

(51) Int. Cl.
C07C 27/00 (2006.01)
C07C 29/00 (2006.01)

(52) U.S. Cl.
USPC ........................................................ 568/861

(58) Field of Classification Search
USPC ........................................................ 568/861
See application file for complete search history.

(56) References Cited

U.S. PATENT DOCUMENTS

| | | | | |
|---|---|---|---|---|
| 7,767,867 B2 * | 8/2010 | Cortright | ...................... | 568/861 |
| 7,960,594 B2 * | 6/2011 | Zhang et al. | .................. | 568/861 |
| 8,222,462 B2 * | 7/2012 | Kalnes et al. | ................. | 568/852 |
| 8,222,463 B2 * | 7/2012 | Kalnes et al. | ................. | 568/852 |
| 8,222,464 B2 * | 7/2012 | Kalnes et al. | ................. | 568/852 |
| 8,222,465 B2 * | 7/2012 | Kalnes et al. | ................. | 568/852 |
| 8,323,937 B2 * | 12/2012 | Zhang et al. | .................. | 435/158 |
| 8,324,433 B2 * | 12/2012 | Zhang et al. | .................. | 568/861 |
| 8,338,326 B2 * | 12/2012 | Zhang | .......................... | 502/177 |
| 2010/0256424 A1 * | 10/2010 | Zhang et al. | .................. | 568/861 |

OTHER PUBLICATIONS

"Direct Catalytic Conversion of Cellulose into Ethylene Glycol Using Nickel-Promoted Tungsten Carbide Catalysts," Na Ji et al. Angew. Chem. Int. Ed. 2008, 47, pp. 8510-8513.*

* cited by examiner

*Primary Examiner* — Patricia L Hailey

(74) *Attorney, Agent, or Firm* — Novick, Kim & Lee, PLLC; Allen Xue

(57) ABSTRACT

Tungsten carbide catalysts are used in preparation of ethylene glycol by hydrogenating degradation of cellulose. The catalyst includes tungsten carbide as main catalytic active component, added with small amount of one or more transition metals such as nickel, cobalt, iron, ruthenium, rhodium, palladium, osmium, iridium, platinum, and copper as the second metal, supported on one or more porous complex supports such as active carbon, alumina, silica, titanium dioxide, silicon carbide, zirconium oxide, for conversion of cellulose to ethylene glycol. The catalyst realizes high efficiency, high selectivity, and high yield in the conversion of cellulose to ethylene glycol at the temperature of 120-300° C., hydrogen pressure of 1-10 MPa, and hydrothermal conditions. Compared to the existing industrial synthetic method of ethylene glycol using ethylene as feedstock, the invention has the advantages of using renewable raw material resources, environment friendly process, and excellent atom economy.

20 Claims, No Drawings

METHODS OF USING TUNGSTEN CARBIDE CATALYSTS IN PREPARATION OF ETHYLENE GLYCOL

This is a divisional application of application Ser. No. 12/734,763, filed May 18, 2010, which is a National Stage of International Application of PCT/CN2008/072892, filed Oct. 31, 2008, both of which are incorporated herein by reference.

BACKGROUND OF THE PRESENT INVENTION

1. Field of Invention

The present invention relates to a method of synthesizing ethylene glycol, and more particularly to tungsten carbide catalysts and the preparation, as well as the application in the reaction of preparing ethylene glycol by hydrogenating degradation of cellulose.

2. Description of Related Arts

Ethylene glycol is an important liquid energy fuel and very important feed for polyester synthesis. For example, Ethylene glycol is used for synthesis of polyethylene terephthalate (PET) and polyethylene naphthalate (PEN). It is also used as antifreeze, lubricants, plasticizers, surface active agent, etc. Thus it is an organic chemical material with wide applications. In recent years, its demand maintains a growth rate of 6~7% world widely. China has a huge consumption of ethylene glycol. In 2005, the market demand is 5 million tons, accounting for 25% of the world's total production, nearly 80% of which had to be imported. Ethylene glycol is one of China's "Ten key imported products".

Currently, industrial production of ethylene glycol is mainly depending on petroleum as the raw material. The ethylene glycol is produced via ethylene oxidation to form the epoxyethane, followed with hydration to form the final product. [Reference 1: Shen, Ju-hua, Overview of ethylene glycol production, Chemical Technology Market, 2003, 26, (6), 12-15. Reference 2: Process for preparing ethanediol by catalyzing epoxyethane hydration, Patent No. CN1463960-A; CN1204103-C]. This method consumes non-renewable petroleum resources. Also the producing process includes steps of selective oxidation and epoxidation, which confronts many technique difficulties, such as low efficiency, large amount of by-products, high material consumption and pollution.

Using biomass to prepare ethylene glycol can reduce human's dependence on the fossil energy resources, because it is environment friendly and contributing to the sustainable development of the world. Currently the research of biomass conversion to ethylene glycol mostly focuses on the raw materials such as starch, glucose, sucrose, and sugar alcohols. [Reference 3: Process for the preparation of lower polyhydric alcohols, U.S. Pat. No. 5,107,018. Reference 4: Preparation of lower polyhydric alcohols, U.S. Pat. No. 5,210,335.]. These raw materials themselves are food for mankind, so that using them to prepare chemicals will cause the conflict between survival and development of the mankind. In contrast, cellulose is the largest renewable biomass with rich resources but indigestible for human being, such as agricultural production, remaining straw and forestry wastes, so that it is abundant and cheap. The use of cellulose to prepare ethylene glycol enables a new synthetic method to obtain high value products with low cost, meanwhile this will not affect the food supply. In addition, cellulose is formed by polycondensation of glucose units via glycosidic bonds, containing a large number of hydroxyl. In the process of cellulose conversion to ethylene glycol, the hydroxyl is fully retained, so that this transformation process has very high atom economy. Thus, the conversion of cellulose to ethylene glycol has a number of significant advantages unmatched by many other production methods.

However, because the structure of cellulose is much more stable than other biomass, it is a considerable challenge to convert cellulose into small molecule polyols with high efficiently and high selectivity. According to the survey of current literature, there is no report of any works for the cellulose conversion into ethylene glycol with high efficiency and high selectivity with tungsten carbide catalysts.

SUMMARY OF THE PRESENT INVENTION

The main object of the present invention is to provide a kind of tungsten carbide catalysts and their preparation and application in production of ethylene glycol from cellulose by hydrogenating degradation. Cellulose is catalytically converted into ethylene glycol under hydrothermal hydrogenating conditions, with high efficiency and high selectivity.

In order to accomplish the above object, the present invention provides a kind of catalysts for the catalytic conversion of cellulose to ethylene glycol, which is expressed as: $A\text{-}W_xC/B$. Wherein the catalytic active component is $A\text{-}W_xC$. A is one or more metallic elements selected from the group consisting of nickel, cobalt, iron, ruthenium, rhodium, palladium, osmium, iridium, platinum, and copper. $W_xC$ is tungsten carbides, wherein $1 \le x \le 2$. In the catalyst, the total loading of catalytic-active metal is 2-85 wt %. The loading of A is 0.05-30 wt %, and the loading of W is 1-80 wt %. B is a porous support, which comprises one or more complexes selected from the group consisting of active carbon, alumina, silica, titanium oxide, silicon carbide, zirconium oxide.

The catalyst is loaded on the support by impregnating salt solutions of catalytic active components. The loading of tungsten is preferably 10-60 wt %, and the loading of the second metal A is preferably 0.1-5 wt %.

The catalyst precursor obtained by impregnation is dried at 100-160° C., and then heated in hydrogen or methane/hydrogen (methane concentration in mixed gas is 10-100% v/v) at 600-900° C. for temperature-programmed carburization. The preferred temperature is between 700-800° C., and the atmosphere is hydrogen or methane/hydrogen (methane concentration in mixed gas is 20% v/v), carburization time is no less than 1 hour.

The reaction conditions for the catalytic conversion of cellulose into ethylene glycol are described as follows: the hydrogenating degradation of cellulose is performed in a sealed reactor, the mass ratio of cellulose to water is 1:200-1:5, the mass ratio of cellulose to catalyst is 1:1-30:1, the initial pressure of hydrogen filled in the reactor at room temperature is 1-10 MPa, reaction temperature is 120-300° C., and the reaction time is 10 min-24 h.

The present invention has the following advantages:

1. Cellulose has the most abundant production in nature, originating from wide sources such as wood, cotton, corn stover, and crop straw. Using it to prepare ethylene glycol is of low cost. Moreover, compared to the existing industrial process for the synthesis of ethylene glycol which consumes ethylene as feed, the present invention does not rely on fossil energy resources, and has the advantages of using renewable raw material and being consistent with sustainable development.

2. The catalyst cost is low, because that tungsten carbide is used as the main catalytic active component, and a small amount of one or several transition metals such as nickel, cobalt, iron, ruthenium, rhodium, palladium, osmium, iridium, and platinum are added as the second component.

3. The process has very good atom economy, because that the carbon, hydrogen and oxygen atoms of the cellulose molecules are very highly reserved after the catalytic degradation.

4. The hydrogenating degradation of cellulose is preformed under hydrothermal conditions, so that the reaction system is environment friendly, and pollution free. Because water is used as reaction medium, meanwhile no any inorganic acids or bases is involved, the usual environmental pollution problems is avoided in the cellulose degradation process.

5. The catalytic process has high yield and selectivity for ethylene glycol. At optimal reaction conditions, the yield of ethylene glycol can be over 60%, which promises good application prospects.

These and other objectives, features, and advantages of the present invention will become apparent from the following detailed description, the accompanying drawings, and the appended claims.

DETAILED DESCRIPTION OF THE PREFERRED EMBODIMENT

Example 1

Preparation of Ni—$W_2C$/AC catalyst: the ammonium metatungstate and nickel nitrate are mixed at tungsten/nickel weight ratio of 15:1 to obtain a mixed solution, wherein the mass concentration of ammonium metatungstate is 0.4 g/ml. Then, active carbon (AC) is impregnated with the mixed solution. After drying at 120° C. for 12 hours, the catalyst precursor is heated in $H_2$ atmosphere for temperature-programmed carburization. The detailed reaction process is as follows: 1.0 g of the catalyst precursor is loaded in quartz reactor and heated from room temperature to 400° C. in 1 hour, and then to 700° C. at the rate of 1° C./min and maintained for 1 hour for carburization. The hydrogen flow rate is 60 ml/min. The obtained Ni—$W_2C$/AC catalyst with the tungsten loading of 30 wt % and nickel loading of 2 wt % is expressed as Ni—$W_2C$/AC (2 wt % Ni-30 wt % $W_2C$).

With the same condition except changing the concentration of the ammonium metatungstate and nickel nitrate in the impregnating solution, or by multiple impregnation, catalysts with different loadings of catalytic active component can be obtained, wherein the composition is as follow: a Ni—$W_2C$/AC catalyst with nickel loading of 2 wt %, tungsten loading of 5 wt %, 10 wt %, 15 wt %, 60 wt %, or 80 wt %, respectively, as well as a Ni—$W_2C$/AC catalyst with tungsten loading of 30 wt %, nickel loading of 0.05 wt %, 0.2 wt %, 5 wt %, 10 wt %, or 30 wt %, respectively.

Example 2

Preparation of Ni—$W_xC$/AC catalyst: the process is similar to the example 1. The difference is that the temperature is 850° C. to obtain a Ni—$W_xC$/AC catalyst with tungsten loading of 30 wt % and nickel loading of 2 wt %, wherein $W_xC$ is a mixed crystalline phases of $W_2C$ and WC, $1<x<2$, expressed as Ni—$W_xC$/AC (2 wt % Ni-30 wt % $W_xC$).

Example 3

Preparation of $W_xC$/AC catalyst: the process is similar to the example 1. The difference is only ammonium metatengstate is used to obtain the catalyst precursor without adding nickel nitrate, and the carburization temperature is 800° C. in order to obtain $W_2C$/AC catalyst. Otherwise, a higher carburization temperature of 850° C. is set to obtain $W_xC$/AC catalyst, which is a mixed crystalline phases of $W_2C$ and WC, $1<x<2$.

Example 4

Preparation of Ru—$W_2C$/AC catalyst: impregnate the sample of $W_2C$/AC as prepared in embodiment 3 with $RuCl_3$ solution, then dry it at 120° C. and reduce it at 350° C. for 2 h in hydrogen. The Ru—$W_2C$/AC (1 wt % Ru-30 wt % $W_2C$) is obtained with 1% loading of Ru and 30 wt % loading of $W_2C$.

Example 5

Preparation of Co—$W_2C$/AC catalyst: the process is similar to the example 1, the difference is using cobalt nitrate instead of nickel nitrate to obtain the catalyst precursor. In the catalyst, the W loading is 30 wt % and the Co loading is 2 wt %, the catalyst of Co—$W_2C$/AC is obtained.

Example 6

Preparation of Fe—$W_2C$/AC catalyst: the process is similar to the example 1. The difference is using iron nitrate instead of nickel nitrate to obtain the catalyst precursor. In the catalyst, the W loading is 30 wt % and the Fe loading is 2 wt %, the catalyst of Fe—$W_2C$/AC is obtained.

Example 7

Preparation of Pt—$W_2C$/AC catalyst: the process is similar to the example 1. The difference is using chloroplatinic acid instead of nickel nitrate to obtain the precursor. In the catalyst, the W loading is 30 wt % and the Pt loading is 2 wt %, the catalyst of Fe—$W_2C$/AC is obtained.

Example 8

Preparation of Ni—WC/$Al_2O_3$ catalyst: the process is similar to the example 1. The difference is the support is alumina instead of active carbon. Meanwhile, the carburization atmosphere is $CH_4$/$H_2$ (volume ratio 1:4) instead of hydrogen. In the catalyst, the W loading is 30 wt % and the Ni loading is 2 wt %. The catalyst of Ni—WC/$Al_2O_3$ is obtained with the WC phase formation.

Example 9

Preparation of Ni—WC/$SiO_2$ catalyst: the process is similar to the example 1, the difference is the support is silica instead of active carbon. At the same time, the carburization atmosphere is $CH_4$/$H_2$ (methane concentration of 20% v/v), instead of hydrogen. In the catalyst, the W loading is 30 wt % and the Ni loading is 2 wt %. The catalyst Ni—WC/$SiO_2$ is obtained with the WC phase formation.

Example 10

Cellulose conversion experiment: 1.0 g of cellulose, 0.3 g of Ni—$W_2C$/AC catalyst, and 100 ml of water are charged into 200 ml reactor. Then, hydrogen is filled in the reactor to 5 MPa after three times replacement of the gas therein. The reaction is performed at 240° C. for 30 min under stirring at 500 rpm. After the reaction, the liquid products are analyzed with a high-performance liquid chromatography (HPLC) equipped with a calcium ion-exchange column to determine the ethylene glycol concentration. The cellulose conversion is calculated based on the dried weight of the remaining solid. The liquid production yield is calculated by the equation: yield (%)=(the products weight)/(cellulose weight)×100%. The production yields only include the target products, which are ethylene glycol and hexahydric alcohol (including sorbitol and mannitol). The yields of other liquid products, including propylene glycol, erythritol, unknown components, and gas products ($CO_2$, $CH_4$, $C_2H_6$, etc.) are not calculated.

Example 11

The comparison of catalytic performance of Ni—$W_2$C/AC (2 wt % Ni-30 wt % $W_2$C), Ni—$W_x$C/AC (2 wt % Ni-30 wt % $W_x$C, 1<x<2) with $W_2$C/AC (30 wt %), $W_x$C/AC (30 wt %, 1<x<2), and Ni/AC (2 wt %), see Table 1. The reaction condition is the same as example 10.

TABLE 1

The comparison of catalytic performance of Ni—$W_2$C/AC, Ni—$W_x$C/AC $W_2$C/AC, and $W_x$C/AC, Ni/AC

| Catalyst | Cellulose conversion % | Ethylene glycol yield % | hexahydric alcohol yield % | Others % |
|---|---|---|---|---|
| Ni—$W_2$C/AC | 100 | 62 | 6 | 32 |
| Ni—WxC/AC | 100 | 59 | 7 | 34 |
| $W_2$C/AC | 98 | 27 | 2 | 69 |
| WxC/AC | 96 | 24 | 3 | 69 |
| Ni/AC | 68 | 5 | 5 | 58 |

As illustrated in the table 1, nickel promoted tungsten carbide catalyst has a very excellent yield of ethylene glycol.

Example 12

The comparison of the performance of catalysts with different second metals: Ni—$W_2$C/AC (2 wt % Ni-30 wt % $W_2$C), Ru—$W_2$C/AC (1 wt % Ru-30 wt % $W_2$C), Co—$W_2$C/AC (2 wt % Co-30 wt % $W_2$C), Fe—$W_2$C/AC (2 wt % Fe-30 wt % $W_2$C), and Pt—$W_2$C/AC (1 wt % Pt-30 wt % $W_2$C), see Table 2. The reaction condition is the same as example 10.

TABLE 2

The comparison of the performance of catalysts with different second metals: Ni—$W_2$C/AC, Co—$W_2$C/AC, Fe—$W_2$C/AC, and Pt—$W_2$C/AC

| Catalyst | Cellulose conversion % | Ethylene glycol yield % | hexahydric alcohol yield % | Others % |
|---|---|---|---|---|
| Ni—$W_2$C/AC | 100 | 62 | 6 | 32 |
| Ru—$W_2$C/AC | 100 | 60 | 7 | 33 |
| Co—$W_2$C/AC | 82 | 41 | 13 | 31 |
| Fe—$W_2$C/AC | 73 | 29 | 6 | 38 |
| Pt—$W_2$C/AC | 100 | 48 | 8 | 44 |

As illustrated in the Table 2, all transition metal promoted tungsten carbide catalysts have very excellent yield of ethylene glycol, wherein Ni—$W_2$C/AC catalyst has a yield of ethylene glycol up to 62%.

Example 13

The comparison of the performance of catalysts with different supports: Ni—$W_2$C/AC (2 wt % Ni-30 wt % $W_2$C), Ni—WC/$Al_2O_3$ (2 wt % Ni-30 wt % $W_2$C), and Ni—$W_2$C/$SiO_2$ (2 wt % Ni-30 wt % $W_2$C), see Table 3. The reaction condition is the same as example 10.

TABLE 3

The comparison of the performance of catalysts with different supports: Ni—$W_2$C/AC, Ni—WC/$Al_2O_3$, and Ni—$W_2$C/$SiO_2$

| Catalyst | Cellulose conversion % | Ethylene glycol yield % | hexahydric alcohol yield % | Others % |
|---|---|---|---|---|
| Ni—$W_2$C/AC | 100 | 62 | 6 | 32 |
| Ni—WC/$Al_2O_3$ | 95 | 35 | 8 | 52 |
| Ni—WC/$SiO_2$ | 85 | 38 | 14 | 33 |

As illustrated in the Table 3, all nickel tungsten carbide catalysts with different supports have good yield of ethylene glycol.

Example 14

The comparison of the cellulose catalytic conversion over catalyst Ni—$W_2$C/AC (2 wt % Ni-30 wt % $W_2$C) at different temperatures, see Table 4. The reaction condition is the same as example 10 except the temperature.

TABLE 4

The comparison of the cellulose catalytic conversion over catalyst Ni—$W_2$C/AC at different temperatures.

| Reaction temperature ° C. | Cellulose conversion % | Ethylene glycol yield % | hexahydric alcohol yield % | Others % |
|---|---|---|---|---|
| 130 | 25 | 8 | 6 | 11 |
| 190 | 54 | 26 | 8 | 20 |
| 220 | 100 | 58 | 5 | 37 |
| 240 | 100 | 62 | 6 | 32 |
| 250 | 100 | 48 | 9 | 43 |
| 270 | 100 | 15 | 6 | 79 |

As illustrated in the Table 4, nickel tungsten carbide catalyst has a very excellent yield of ethylene glycol within a range of temperatures. The preferred temperature is about 220-250° C.

Example 15

The comparison of the cellulose catalytic conversion over catalyst Ni—$W_2$C/AC (2 wt % Ni-30 wt % $W_2$C) with different reaction time, see Table 5. The reaction condition is the same as example 10 except the reaction time.

TABLE 5

The comparison of the cellulose catalytic conversion over catalyst Ni—$W_2$C/AC with different reaction time.

| Reaction time | Cellulose conversion % | Ethylene glycol yield % | hexahydric alcohol yield % | Others % |
|---|---|---|---|---|
| 10 min | 54 | 24 | 2 | 28 |
| 30 min | 100 | 62 | 6 | 32 |
| 3 h | 100 | 51 | 13 | 36 |
| 5 h | 100 | 24 | 6 | 70 |
| 24 h | 100 | 16 | 4 | 80 |

As illustrated in the Table 5, nickel tungsten carbide catalyst has a very excellent yield of ethylene glycol within a range of reaction time. The preferred reaction time is 30 min-3 h.

Example 16

The comparison of the cellulose catalytic conversion over catalyst Ni—$W_2$C/AC (2 wt % Ni-30 wt % $W_2$C) at different hydrogen pressures, see Table 6. The reaction condition is the same as example 10 except the hydrogen pressure.

TABLE 6

The comparison of the cellulose catalytic conversion over catalyst Ni—W₂C/AC at different hydrogen pressures.

| Hydrogen pressure Mpa | Cellulose conversion % | Ethylene glycol yield % | hexahydric alcohol yield % | Others % |
|---|---|---|---|---|
| 2 | 31 | 6 | 17 | 8 |
| 3 | 82 | 32 | 26 | 24 |
| 5 | 100 | 62 | 6 | 32 |
| 6 | 100 | 54 | 14 | 32 |
| 9 | 100 | 28 | 18 | 54 |

As illustrated in the Table 6, nickel tungsten carbide catalyst has a very excellent yield of ethylene glycol within a range of hydrogen pressure. The preferred hydrogen pressure is 3-6 MPa.

Example 17

The comparison of the cellulose catalytic conversion over catalyst Ni—W₂C/AC (30 wt % W₂C) with different nickel loadings, see Table 7. The reaction condition is the same as example 10.

TABLE 7

The comparison of the cellulose catalytic conversion over catalyst Ni—W₂C/AC with different nickel loadings.

| Ni content % | Cellulose conversion % | Ethylene glycol yield % | hexahydric alcohol yield % | Others % |
|---|---|---|---|---|
| 0.05 | 95 | 6 | 3 | 86 |
| 0.1 | 98 | 55 | 5 | 38 |
| 2 | 100 | 62 | 6 | 32 |
| 5 | 85 | 42 | 8 | 35 |
| 10 | 40 | 18 | 13 | 9 |
| 30 | 38 | 14 | 14 | 6 |

As illustrated in the Table 7, the nickel loading has a certain effect on the yield of ethylene glycol by using nickel tungsten carbide catalyst. The preferred nickel loading is 0.1-5 wt %.

Example 18

The comparison of the cellulose catalytic conversion over catalyst Ni—W₂C/AC (2 wt % Ni) with different tungsten carbide loadings, see Table 8. The reaction condition is the same as example 10.

TABLE 8

The comparison of the cellulose catalytic conversion over catalyst Ni—W₂C/AC with different tungsten carbide loadings.

| Tungsten loading wt % | Cellulose conversion % | Ethylene glycol yield % | hexahydric alcohol yield % | Others % |
|---|---|---|---|---|
| 5 | 54 | 22 | 4 | 28 |
| 10 | 76 | 43 | 6 | 27 |
| 15 | 83 | 58 | 7 | 18 |
| 30 | 100 | 62 | 6 | 32 |
| 60 | 100 | 63 | 12 | 25 |
| 80 | 85 | 35 | 13 | 37 |

As illustrated in the Table 8, nickel tungsten carbide catalyst can realize a very excellent yield of ethylene glycol within a certain range of tungsten loadings. The preferred loading is 10-60 wt %.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method of catalytic degradation of cellulose, comprising:
    obtaining a mixture comprising cellulose, water, and a catalyst;
    placing the mixture in a reactor filled with hydrogen; and
    keeping the mixture at an elevated temperature for a certain reaction time,
    wherein the catalyst has a formula A-WxC/B, in which component A represents one or more metallic elements chosen from nickel, cobalt, iron, ruthenium, rhodium, palladium, osmium, iridium, platinum, and copper, W represent tungsten, and WxC represents tungsten carbide, wherein $1 \leq x \leq 2$, and
    component B is a porous support chosen from active carbon, alumina, silica, titanium oxide, silicon carbide, zirconium oxide, and mixtures thereof.

2. The method of claim 1, wherein a total loading of A-WxC in said catalyst is 2-85 wt %, a loading of component A in said catalyst is 0.05-30 wt % and a loading of tungsten in said catalyst is 1-80 wt %.

3. The method of claim 2, wherein the loading of tungsten is 10-60 wt % and the loading of component A is 0.1-5 wt %.

4. The method of claim 1, wherein a mass ratio of the cellulose to water is in the range of 1:200 to 1:5.

5. The method of claim 1, wherein a mass ratio of the cellulose to the catalyst is in the range of 1:1 to 30:1.

6. The method of claim 5, wherein a mass ratio of the cellulose to the catalyst is in the range of 10:1 to 20:1.

7. The method of claim 1, wherein the hydrogen pressure in the reactor is in the range of 1 to 10 MPa at room temperature.

8. The method of claim 7, wherein the hydrogen pressure in the reactor is in the range of 3 to 7 MPa at room temperature.

9. The method of claim 1, wherein said elevated temperature is in the range of 120 to 300° C.

10. The method of claim 9, wherein said elevated temperature is in the range of 220 to 250° C.

11. The method of claim 1, wherein said reaction time is in the range of 10 min to 24 hours.

12. The method of claim 11, wherein said reaction time is in the range of 30 min to 6 hours.

13. The method of claim 1, wherein the cellulose is derived from biomass.

14. The method of claim 11, wherein cellulose is degraded to form ethylene glycol.

15. The method of claim 14, wherein the product further comprises hexahydric alcohol.

16. The method of claim 14, wherein the yield of ethylene glycol is larger than about 60%.

17. The method of claim 1, wherein component A represents nickel.

18. The method of claim 17, wherein the loading of nickel ranges from 1-10 wt %.

19. The method of claim 1, wherein component A represents ruthenium.

20. The method of claim 1, wherein component A represents iridium.

* * * * *